(12) United States Patent
Cadwalader (10) Patent No.: US 6,310,355 B1
(45) Date of Patent: Oct. 30, 2001

(54) LIGHTWEIGHT RADIATION SHIELD SYSTEM

(75) Inventor: John A. Cadwalader, Overland Park, KS (US)

(73) Assignee: Worldwide Innovations and Technologies, Inc., Overland Park, KS (US)

( * ) Notice: Subject to any disclaimer, the term of this patent is extended or adjusted under 35 U.S.C. 154(b) by 0 days.

(21) Appl. No.: 09/251,065

(22) Filed: Feb. 18, 1999

(51) Int. Cl.[7] .................................. G21F 3/00; A61B 6/10
(52) U.S. Cl. ........................ 250/515.1; 250/516.1; 250/519.1; 75/415; 428/328
(58) Field of Search ............................. 250/515.1, 516.1, 250/519.1; 75/415; 428/328

(56) References Cited

U.S. PATENT DOCUMENTS

| | | | |
|---|---|---|---|
| 3,419,006 | 12/1968 | King | 128/268 |
| 3,935,099 | 1/1976 | Weaver et al. | 210/43 |
| 4,621,808 | 11/1986 | Orchard et al. | 272/119 |
| 4,938,233 | * 7/1990 | Orrison, Jr. | 128/849 |
| 5,523,581 | 6/1996 | Cadwalader | 250/519.1 |
| 5,525,408 | * 6/1996 | Weir et al. | 428/220 |
| 6,048,379 | * 4/2000 | Bray et al. | 75/229 |
| 6,153,666 | * 11/2000 | Lagace | 523/136 |

* cited by examiner

Primary Examiner—Bruce Anderson
Assistant Examiner—Nikita Wells
(74) Attorney, Agent, or Firm—Foley & Lardner (57) ABSTRACT

A covering or shield attenuating the flux of electromagnetic radiation from an article. The shield includes a matrix, a radiation attenuating material provided in the matrix, and at least one space provided in the matrix. The space reduces the overall weight of the shield. The space can be a variety of shapes, including round, honeycombed, triangular, rectangular, or other configuration.

28 Claims, 7 Drawing Sheets

LIGHTWEIGHT RADIATION SHIELD SYSTEM

CROSS-REFERENCE TO RELATED APPLICATIONS

The following U.S. patent is cross-referenced and incorporated by reference herein: U.S. Pat. No. 4,938,233 issued Jul. 3, 1990 to Orrison, Jr. titled "RADIATION SHIELD."

FIELD OF THE INVENTION

The present invention relates to the attenuation of electromagnetic radiation. More particularly, the present invention relates to an improved lightweight radiation shield or covering.

BACKGROUND OF THE INVENTION

It is well known to use a radiation shield to attenuate or deflect the flux of electromagnetic radiation from a radiation source directed toward an article (e.g., sample, room, human body, or part thereof, etc.). Radiation can be provided from a variety of natural or man-made sources and can be electromagnetic energy at wavelengths of $1.0 \times 10^{-15}$ meters (e.g., cosmic rays) to $1.0 \times 10^6$ meters (e.g., radiation from AC power lines). Radiation can have beneficial or negative effects. Accordingly, it is generally known in the art to shield an article from radiation or to focus the radiation using apparatus such as the radiation shields described in U.S. Pat. No. 4,938,233 issued Jul. 3, 1990 to Orrison, Jr. titled "RADIATION SHIELD" and hereby incorporated by reference.

Known radiation shields and focusing devices include generally rigid materials. Radiation shields made from rigid materials effectively attenuate radiation, but are too inflexible for certain applications, such as, radiological procedures. Radiological procedures often require the attenuation of radiation directed toward the thyroid area, male gonadal areas, female gonadal areas, breast area, hands, eyes, etc. Radiation shields made from rigid materials also tend to be heavy in weight.

In an attempt to overcome the shortcomings of rigid radiation shields, flexible radiation shields and focusing devices have been developed to cover non-planar surfaces. Examples of conventional flexible radiation shields comprised of a visco-elastic polymeric matrix charge with an alternating inorganic filler are described in U.S. Pat. No. 4,938,233 issued Jul. 3, 1990 to Orrison, Jr. titled "RADIATION SHIELD". Such known flexible radiation shields and focusing devices can be reusable, sterilizable or disposable. Conventional flexible radiation shields and focusing devices can be heavy in weight and costly to construct. Generally, the attenuating material in the radiation shield includes dense elements, such as, barium, lead, etc. that can be significantly responsible for the overall weight of the shield. Further, some conventional flexible shields do not provide suitable insulation for the article being shielded from the radiation.

Accordingly, there is a need for a lightweight covering or shield for attenuating the flux of electromagnetic radiation directed toward an article. There is also a need for a method of making a lightweight shield for attenuating the flux of electromagnetic radiation directed toward an article. There is further still a need for a lightweight, flexible covering or shield.

SUMMARY OF THE INVENTION

The present invention relates to a shield or covering for attenuating the flux of electromagnetic radiation directed toward an article. The shield includes a matrix, a radiation attenuating material, and at least one space provided in the matrix. The matrix is charged with the attenuating material.

The present invention further relates to a method for making a covering or a shield for attenuating the flux of electromagnetic radiation directed toward an article. The method includes providing a matrix including a radiation attenuating material, and providing at least one space in the matrix.

The present invention further relates to a shield or covering for attenuating the flux of electromagnetic radiation. The shield includes a matrix comprising insulating material and a radiation attenuating material. The matrix has at least one space. The space reduces the weight of the shield without appreciably reducing the attenuating characteristics of the shield.

DESCRIPTION OF THE FIGURES

The present invention will be hereafter described with reference to the accompanying drawings, wherein like materials denote like elements, and.

DETAILED DESCRIPTION OF THE PREFERRED EXEMPLARY EMBODIMENTS

Figure 1A:
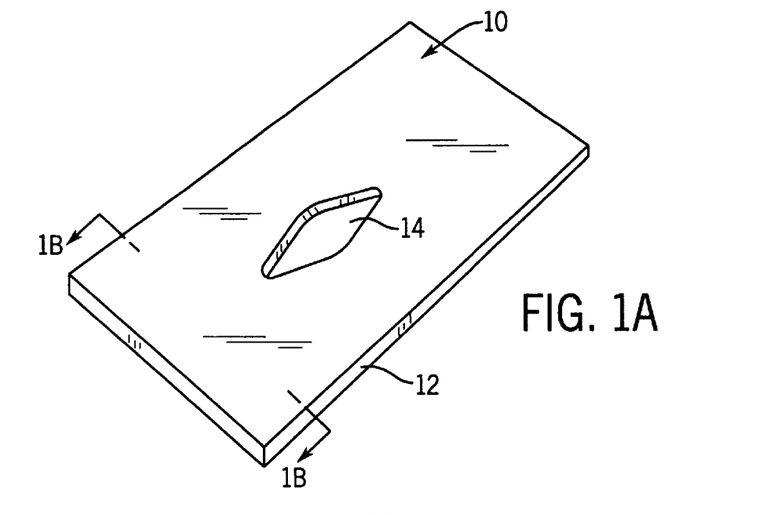
FIG. 1A is a perspective view of a covering or shield according to an exemplary embodiment of the present invention.
Figure 1B:
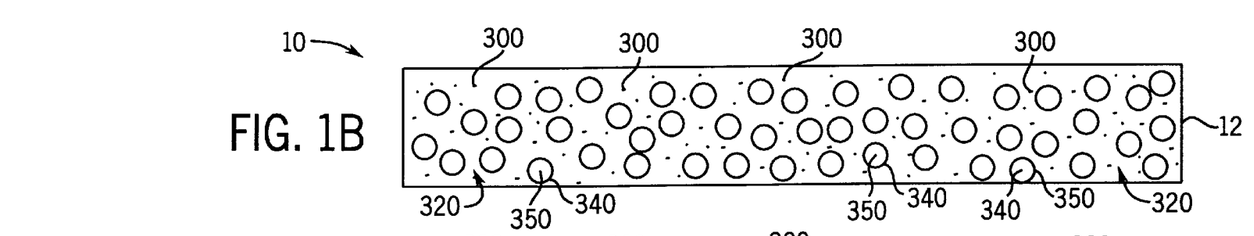
FIG. 1B is cross-sectional view of the shield of FIG. 1A taken along line 1B—1B in FIG. 1A according to another exemplary embodiment of the presentation.

FIG. 1A shows a covering or shield for attenuating and focusing electromagnetic radiation (shown as a shield 10 having a wall 12 and an aperture 14) according to an exemplary embodiment of the present invention. FIG. 1B shows shield 10 including a matrix 320 provided or charged with a radiation attenuating material (shown as an attenuant 300). Matrix 320 includes a space 340 in which a filling-material (shown as a gas 350) can be inserted.

Shield 10 attenuates electromagnetic radiation (e.g., gamma rays, x-rays, etc.) and has an attenuation factor similar to the attenuation factor of other shields that do not include spaces such as space 340. Shield 10 is lighter in weight than conventional shields due to space 340. According to an alternative embodiment of the present invention, the filling material (e.g., gas 350 in space 340) can include a lightweight material such as helium, foam, liquid, etc. According to other alternative embodiments, the filling material can include a heavier material such as wax, atmospheric air, lead, barium, water, etc. According to a particularly preferred embodiment, the filling material is paraffin.

According to an alternative or preferred embodiment as shown in FIGS. 1B through 1E, matrix 320 of shield 10 includes space 340, which can be in a variety of shapes or configurations. Space 340 can also be of diverse sizes. The shapes, configurations, and sizes of spaces 340 can be chosen for particular application parameters and system requirements. For example, spaces 340 can be smaller to attenuate higher frequency radiation. In another example, space 340 can be shaped to meet specific load or strength requirements of the particular application. Thus, the specific orientation of space 340 can be designed for particular applications. A variety of procedures may be used to provide the matrix with spaces. According to one embodiment, the matrix is heated, then cooled (e.g., cured) so that spaces are formed in the matrix absent further processing. According to a particularly preferred embodiment, the matrix is subjected to vacuum pressure such that only a portion of the spaces in the matrix is removed.

Figure 1C:
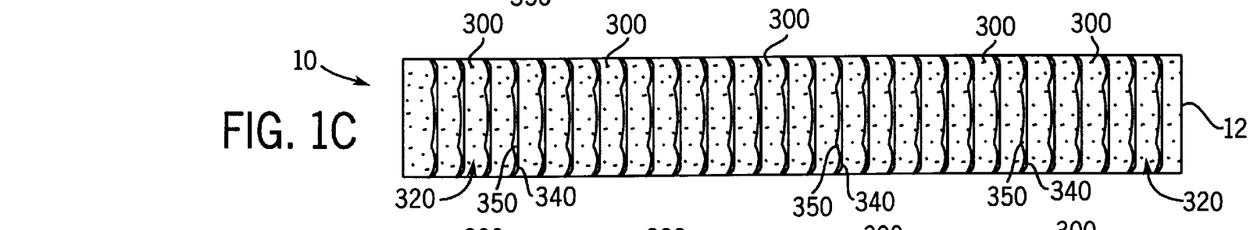
FIG. 1C is cross-sectional view of the shield of FIG. 1A taken along line 1B—1B in FIG. 1A according to an alternative embodiment of the present invention.
Figures 1D, 1E:
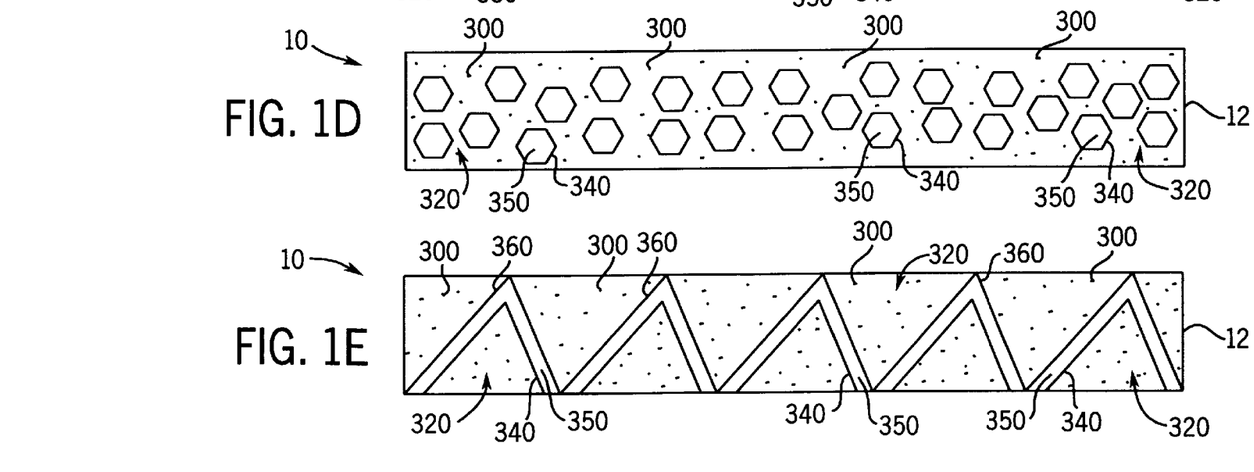
FIG. 1D is cross-sectional view of the shield of FIG. 1A taken along line 1B—1B in FIG. 1A according to an alternative embodiment of the present invention.
FIG. 1E is cross-sectional view of the shield of FIG. 1A taken along line 1B—1B in FIG. 1A according to an alternative embodiment of the present invention.

According to an alternative embodiment as shown in FIG. 1B, matrix 320 is constructed of urethane foam having small bubble-shaped spaces. According to other alternative embodiments as shown in FIGS. 1C through 1E, space 340 can be of a variety of shapes including but not limited to a six-sided honeycomb (see FIG. 1D), a vertical groove (see FIG. 1C), a horizontal slot (not shown), a zigzag groove (not shown), a random shape (not shown), etc. According to other alternative embodiments as shown in FIG. 1E, space 340 is formed by protrusions 360 of various shapes (e.g., fingered, U-shaped, V-shaped, baffled, etc.). Not intending to be limited by theory, it is believed that the shape of the space may provide additional strength and may allow for a somewhat orderly structure of the matrix.

According to other alternative embodiments, matrix 320 is constructed of an insulating material such as fiberglass, wool, asbestos, spun plastic, spun metal, foam, insulating foam, urethane foam, etc. The insulating material provides spaces, like space 340, within the shield. The insulating material or foam can be capable of being blown, injected or dispersed into a fixed space, such as the inside walls of the shield. The insulating material or foam can be capable of hardening (e.g., curing) after a period in the shield or upon a chemical reaction. According to other alternative embodiments, the matrix is a sponge (e.g., porous rubber, cellulose, etc.).

According to an alternative embodiment, various fragrances can be provided within the matrix. According to an alternative embodiment, matrix 320 can be preformed such that it can readily be deposited (e.g., blown from a storage container) into the shield.

According to another alternative embodiment of the present invention, matrix 320 is constructed of a viscoelastic polymeric matrix of the type described in U.S. Pat. No. 4,938,233 issued Jul. 3, 1990 to Orrison, Jr. titled "RADIATION SHIELD". Shield 10 with space 340 (see FIGS. 1A and 1B) has the same attenuation characteristics as the shield disclosed in U.S. Pat. No. 4,938,233 which does not include space 340.

According to other alternative embodiments, the polymeric matrix includes silicones and urethanes (polyester, polyether and polybutadiene-based), rubbers (both natural and synthetic) as well as various gels. Examples of compositions that can be used include those described in U.S. Pat. No. 3,419,006 issued Dec. 31, 1968 to King titled "NOVEL DRESSING AND USE THEREOF" and U.S. Pat. No. 3,935,099 issued Jan. 27, 1976 to Weaver et al. titled "METHOD OF REDUCING WATER CONTENT OF EMULSIONS, SUSPENSIONS, AND DISPERSIONS WITH HIGHLY ABSORBENT STARCH-CONTAINING POLYMERIC COMPOSITIONS". Other compositions of interest include polystyrene butadiene block copolymers, (low density) polyethylene, poly (n-butyl methacrylate), polystyrene diluted with tricresyl phosphate, poly (methyl acrylate), poly (n-butyl methacrylate), and various polystyrenes and polyisoprenes, poly (alpha-methylstrene) or the gels including polyacrylonitrides, cellulose trinitrate, or poly (vinyl chloride) in di-2-ethylhexyl phthalate, cellulose tributyrate, cellulose nitrate and gelatin, or cross-linked gels such as poly (beta-hydroxy ethylmethacrylate), provided the same possess the requisite durometer and friction characteristics. Various water-based gels (hydrogels) including those prepared with starch, polyacrylonitrile, polyethylene oxide, polyvinylpyrolidone, hydrophilic urethanes, etc. can also be used. Those skilled in the art who review this disclosure may select other suitable matrix materials meeting the functional attributes required for use in the present invention, thus, the foregoing listing is simply representative of adequate candidates of the polymer matrix.

Matrix 320 can be comprised of an initial polymer selected from the group consisting of visco-elastic vinyl polymers or vinyl acetate copolymers, silicones and urethanes, and mixtures thereof, although other suitable compositions exist. Particularly preferred are vinyl polymers or copolymers. In a highly preferred embodiment, a tincture of iodine is compounded with the initial polymer, regardless of the presence of any iodine salts. A preferred composition in this regard includes a matrix of a plasticized vinyl polymer having a ratio of plasticizer to polymer in the range of about 5:1 to about 32:1. According to other alternative embodiments, the polymeric mix can be compounded, along with any necessary stabilizers, thickening agents, surfactants or the like as set forth more particularly in U.S. Pat. No. 4,621,808 issued Nov. 11, 1986 to Orchard et al. titled "VISCO-ELASTIC WEIGHT", particulate is blended and sufficiently worked to develop uniform distribution, and the composition is cast and allowed to cure, set or polymerize as the case may be.

The polymeric matrix is preferably a visco-elastic material such as a visco-elastic vinyl polymer, vinyl-acetate copolymer, silicone or urethane. A highly preferred visco-elastic polymer is one such as that disclosed in U.S. Pat. No. 4,621,808 issued Nov. 11, 1986 to Orchard et al., and incorporated herein by reference. That composition is a highly plasticized polyvinyl chloride wherein the ratio of plasticizer to resin can vary broadly over the range of from about 5:1 to about 32:1. Preferred plasticizers include dialkyl phthalate, diundecyl phthalate, dioctyl phythalate and duisononyl phthalate. The resultant material is one having suitable characteristics for use as the polymeric matrix in accordance with the present invention. Alternatively, a similar composition, but based on a vinyl-acetate copolymer, can be adapted to the same end.

The matrix is charged with a radiation attenuating filler as described in U.S. Pat. No. 4,938,233 issued Jul. 3, 1990 to Orrison, Jr. titled "RADIATION SHIELD". The attenuating filler (attenuant 300) can be any composition compatible with the matrix and that exhibits radiopacity (i.e., being opaque to various forms of electromagnetic radiation) to the electromagnetic radiation of interest. Attenuating fillers generally include an inorganic salt having a radiopaque cation. The cation is preferably selected from the group consisting of barium, iodine and mixtures thereof, although many other suitable cations exist such as bismuth, uranium and zirconium containing compositions alone or in combination. According to a preferred embodiment, the attenuating filler is a particulate of a barium salt (such as barium sulfate). Not wishing to be limited by theory, it is hypothesized that if the appropriate atomic-numbered attenuating filler is used (e.g., hydrogen, boron, tungsten, etc.), the matrix will attenuate any type of electromagnetic radiation (e.g., x-rays, gamma rays) and/or neutrons. Shield 10 can be configured to protect astronauts, transportation vehicles, satellites, etc. involved in space travel from cosmic radiation. According to a preferred embodiment, the attenuating filler (i.e., barium sulfate) is present in the range of up to about 80% by total weight), more preferably in the range of from about 10% to about 70% and most preferably in the range of from about 20% to about 60%, with less than 0.5% tincture of iodine.

FIGS. 2 through 14B show exemplary coverings or shields for attenuating radiation. Shield 10, with its advantageous matrix 320, shown in FIGS. 1A through 1E can be configured for any of the forms discussed below with reference to FIGS. 2 through 21.

Figures 2, 3:
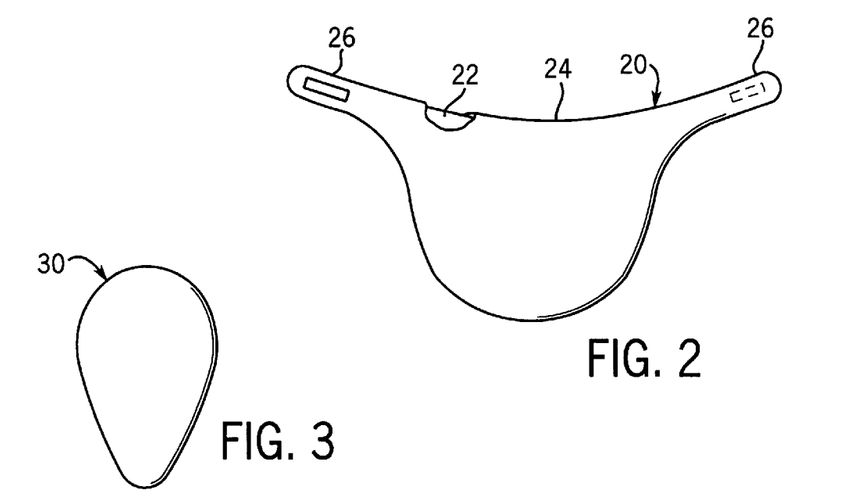
FIG. 2 is a top plan view of a thyroid shield according to an alternative exemplary embodiment of the present invention.
FIG. 3 is a top plan view of a male gonadal shield according to an alternative exemplary embodiment of the present invention.

FIG. 2 shows a thyroid shield 20 according to an alternative exemplary embodiment of the present invention. Shield 20 includes a matrix 22 similar to matrix 320 disposed in a cloth covering 24 that includes fasteners 26.

Figure 4:
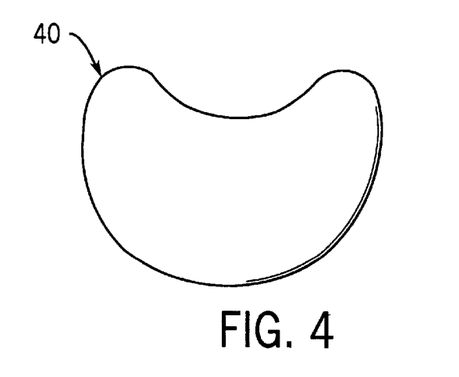
FIG. 4 is a top plan view of a female gonadal shield according to an alternative exemplary embodiment of the present invention.
Figure 5:
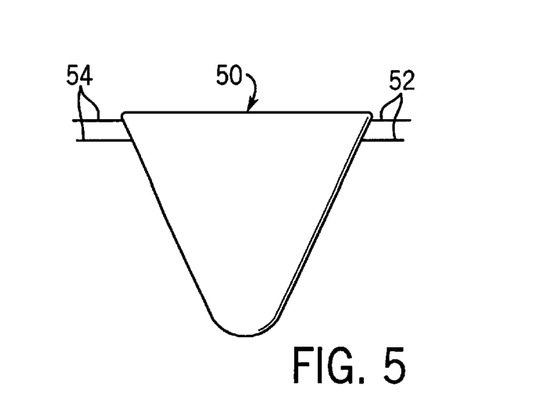
FIG. 5 is a top plan view of a diaper according to an alternative exemplary embodiment of the present invention.

FIG. 3 shows a male gonadal shield 30 according to an alternative exemplary embodiment of the present invention. FIG. 4 shows a female gonadal shield 40 according to an alternative exemplary embodiment of the present invention. FIG. 5 shows a diaper 50 with fasteners 54 and 52 according to an alternative exemplary embodiment of the present invention.

Figure 6A:
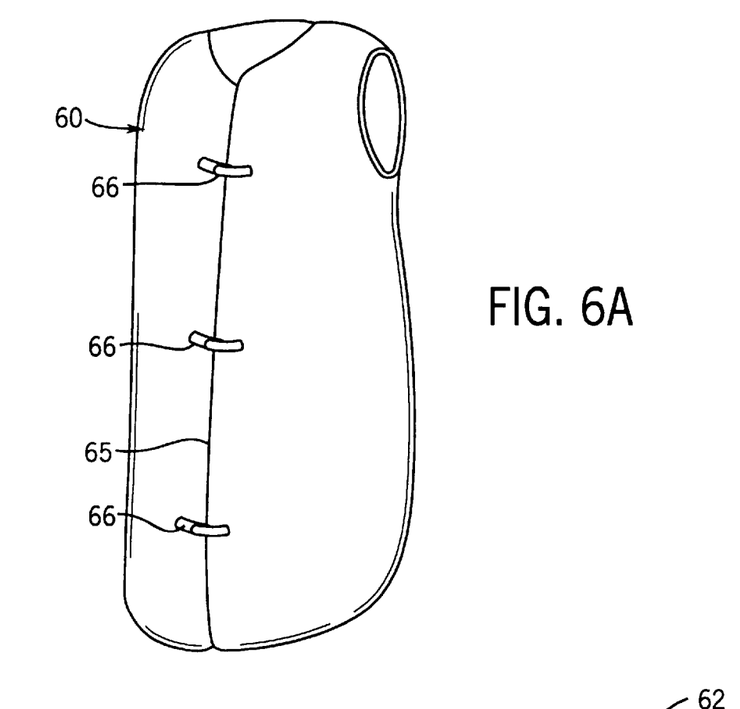
FIGS. 6A and 6B are perspective views of protective aprons according to an alternative exemplary embodiment of the present invention.
Figure 6B:
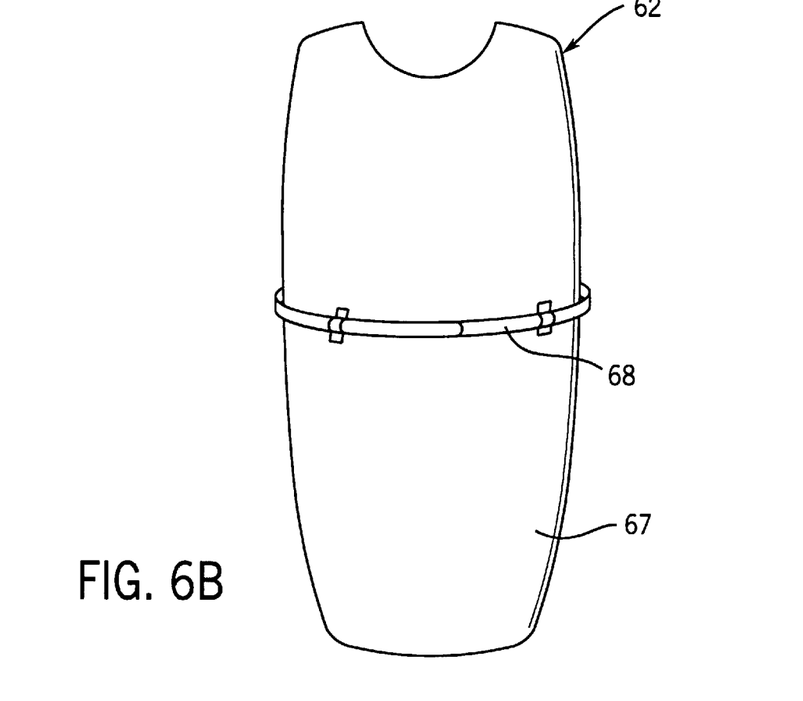
Figure 7:
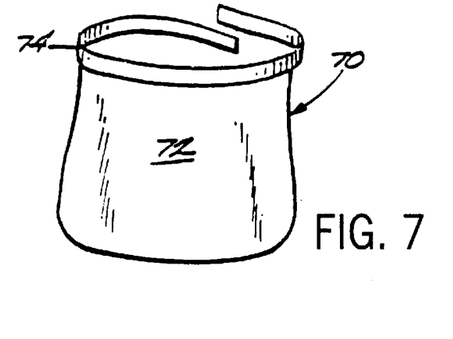
FIG. 7 is a perspective view of a mini-apron according to an alternative exemplary embodiment of the present invention.

FIG. 6A shows an apron 60 with a slit 65 closed by fasteners 66 that can wrap around a patient according to an alternative exemplary embodiment of the present invention. FIG. 6B shows a front shield apron 62, which includes a body panel 67 and a belt fastener 68, according to an alternative exemplary embodiment of the present invention. FIG. 7 shows a mini-apron 70, including a gonadal panel 72 and a fastener 74 which, unlike the aprons of FIGS. 6A and 6B, is designed for only partial (as opposed to full) torso protection according to an alternative exemplary embodiment of the present invention.

Figure 8:
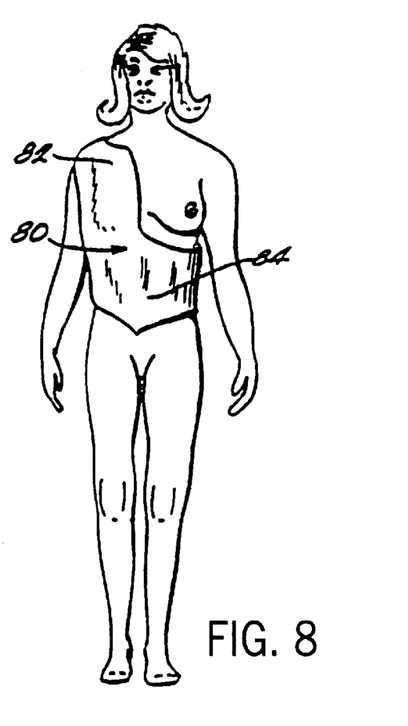
FIG. 8 is a side elevational view of a breast shield according to an alternative exemplary embodiment of the present invention.
Figure 9:
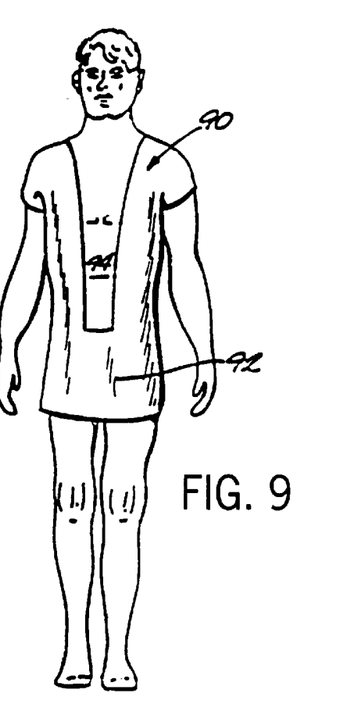
FIG. 9 is a side elevational view of a male patient wearing a scoliosis shield according to an alternative exemplary embodiment of the present invention.

FIG. 8 shows a female patient wearing a breast shield 80 comprised of an upper shield 82 and a lower shield 84 according to an alternative exemplary embodiment of the present invention. FIG. 9 shows a male patient wearing a scoliosis shield 90 according to an alternative exemplary embodiment of the present invention. Shield 90 includes a gonadal shield 92 and an exposed region 94.

Figure 10:
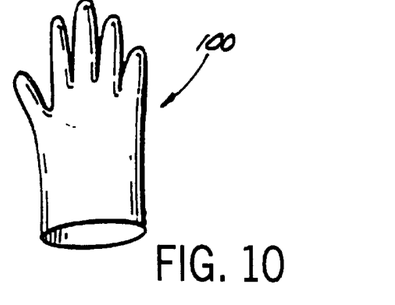
FIG. 10 is a perspective view of a glove shield according to an alternative exemplary embodiment of the present invention.
Figure 11:
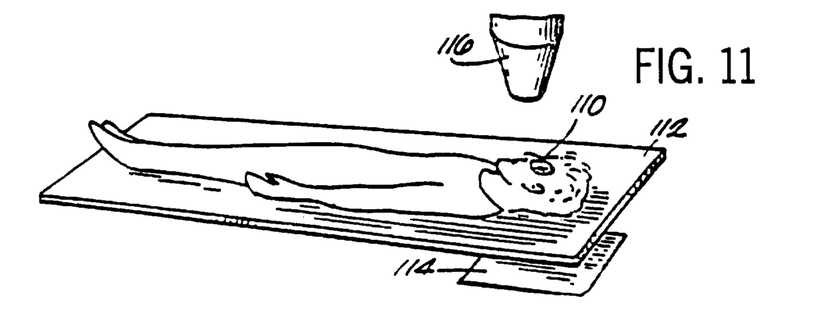
FIG. 11 is a perspective view of an eye disc according to an alternative exemplary embodiment of the present invention.

FIG. 10 shows a protective glove 100 according to an alternative exemplary embodiment of the present invention. FIG. 11 shows a protective eye disc 110 according to an alternative exemplary embodiment of the present invention. Disc 110 is worn about the head and neck of a patient prone on a work surface (shown as a table 112) above a photographic plate 114. The patient is positioned for irradiation under an x-ray tube 116.

Figure 12:
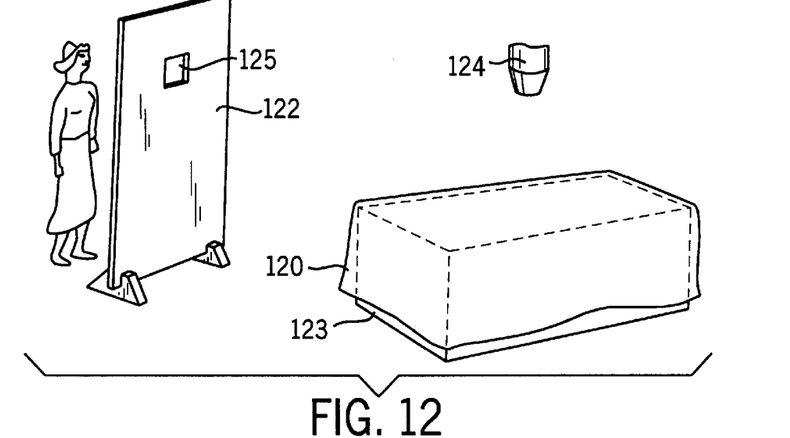
FIG. 12 is a perspective view illustrating a protective barrier according to an alternative exemplary embodiment of the present invention.
Figure 13A:
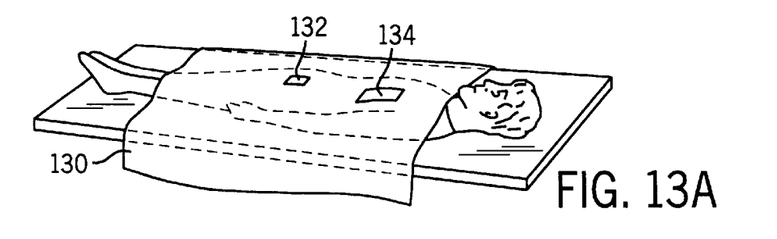
FIGS. 13A and 13B are perspective views of a drape according to an alternative exemplary embodiment of the present invention.
Figure 13B:
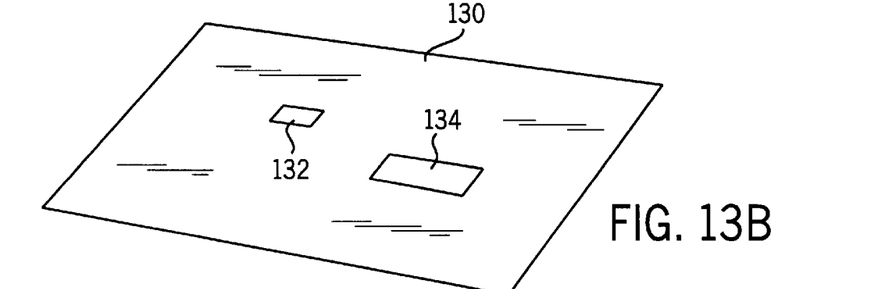
Figure 14A:
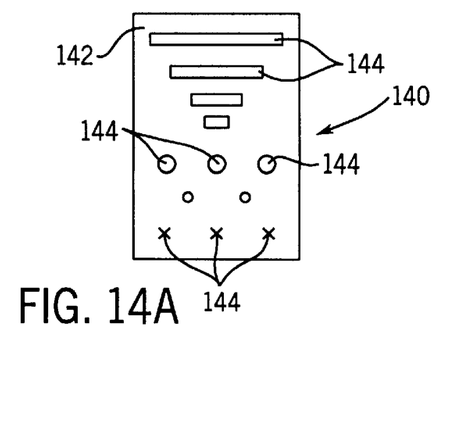
FIGS. 14A and 14B are top plan views of a phantom according to an alternative exemplary embodiment of the present invention.
Figure 14B:
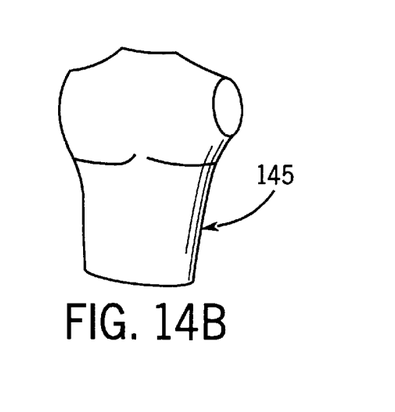

FIG. 12 shows a protective barrier 122 that includes a window 125 according to an alternative exemplary embodiment of the present invention. FIG. 12 also shows a work surface (shown as a table 123) having a protective drape 120. FIGS. 13A and 13B show a protective drape 130. Drape 130 includes a cutout 132 and a neutral material 134 according to an alternative exemplary embodiment of the present invention. FIG. 14A shows a phantom 140 for creating a test pattern for quality control purposes. Phantom 140 includes a rectilinear web 142 including an array of various attenuating elements 144. FIG. 14B shows a phantom 145 for human anatomy according to an alternative exemplary embodiment of the present invention.

Figure 15:
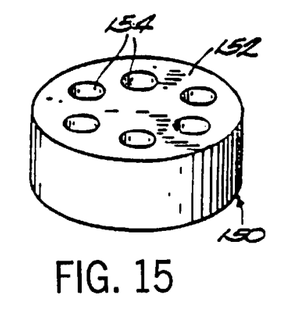
FIG. 15 is a perspective view of a transportation and/or storage device according to an alternative exemplary embodiment of the present invention.

FIG. 15 shows a transportation and/or storage device 150 (e.g., for transportation and/or storage of radionuclides) having apertures 154 in a body 152 according to an alternative exemplary embodiment of the present invention.

Figure 16:
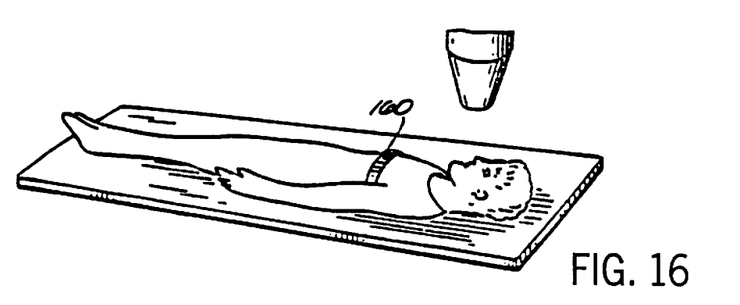
FIG. 16 is a perspective view of a marker according to an alternative exemplary embodiment of the present invention.
Figure 17A:
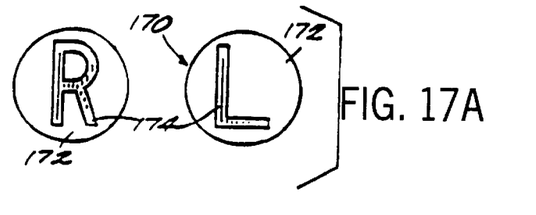
FIGS. 17A and 17B are top plan views of film markers according to an alternative exemplary embodiment of the present invention.
Figure 17B:
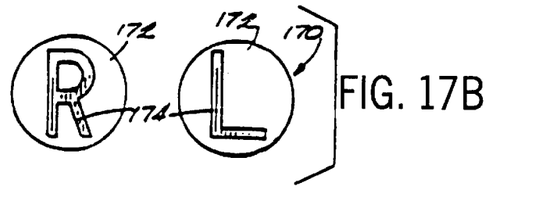

FIG. 16 shows a marker 160 worn by a patient undergoing radiation treatment and/or examination according to an alternative exemplary embodiment of the present invention. FIGS. 17A and 17B show film markers 170, including a support 172 and a designator 174, according to an alternative exemplary embodiment of the present invention.

Figure 18:
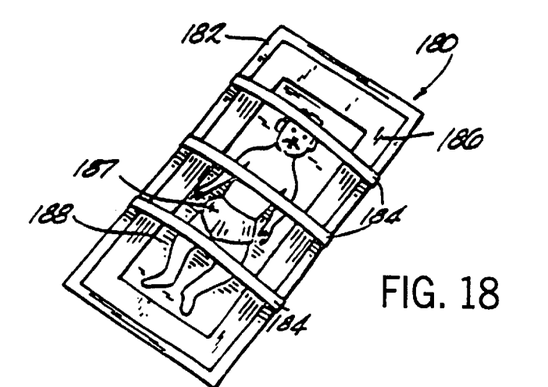
FIG. 18 is a top plan view of an infant stabilization device according to an alternative exemplary embodiment of the present invention.

FIG. 18 shows an infant stabilization device 180 having a frame 182. Device 180 includes straps 184 for securing an infant to a cutout region 188. The infant can wear a diaper 187 of attenuating material. A border 186 of attenuating material surrounds the infant according to an alternative exemplary embodiment of the present invention.

Figures 19A, 19B, 19C, 20, 21:
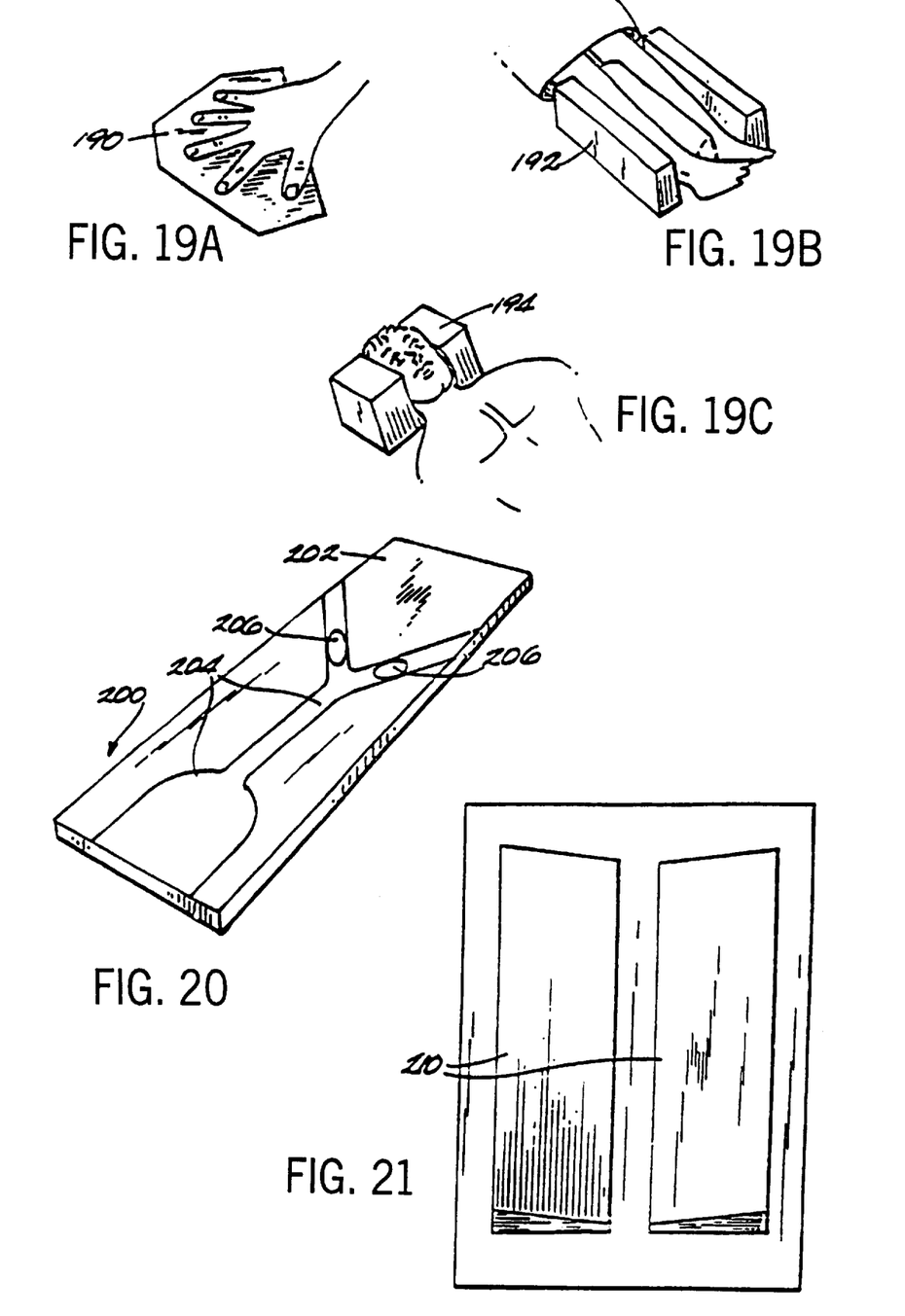
FIGS. 19A through 19C are fragmentary perspective views of a positioning device according to an alternative exemplary embodiment of the present invention.
FIG. 20 is a perspective view of a fluoroscopy table shield according to an alternative exemplary embodiment of the present invention.
FIG. 21 is a top plan view of a density wedge according to an alternative exemplary embodiment of the present invention.

FIGS. 19A through 19C show a variety of patient positioning devices 190, 192 and 194 according to an alternative exemplary embodiment of the present invention. FIG. 20 shows a fluoroscopy table pad 200 (e.g., in this configuration adapted for angiography) according to an alternative exemplary embodiment of the present invention. Pad 200 includes neutral material 204 on a web 202. Web 202 includes cutouts 206. FIG. 21 shows a density wedge 210.

EXAMPLE 1

An experiment was performed to examine the radiation attenuation effectiveness of a covering or shield (shield 10) having a matrix 320 (see FIGS. 1B through 1E). Matrix 320 includes an attenuating filler and a space 340 within matrix 320. Barium-free foam was produced using Campbell's Liquid Shave Cream concentrated soap commercially available from Morris-Flamingo Mfg. Corporation of Danville, Ill. and tap water mixed in the reservoir of a machine used to produce foam, such as the PCS Campbell Lather King, commercially available from Campbell Corporation of Bensenville, Ill. The barium-free foam was placed in a container ("Container A").

Barium-containing foam was produced in the same foam machine by mixing the same soap, the same tap water, and barium sulfate in the amount of approximately 20% barium sulfate by total weight percent of the mixture. The barium-containing foam was placed in a container ("Container B"). Concentrated barium-containing foam was produced in the same foam machine by mixing the same soap, the same tap water, and barium sulfate in the amount of approximately 40% barium sulfate by total weight percent of the mixture. The concentrated barium-containing foam was placed in a container ("Container C"). The same tap water used to make the barium-free foam was placed in a container ("Container D").

Each Container A through D, had a diameter of approximately 4 inches, a height of approximately 1¾ inches, a volume of approximately 22 inches$^3$, was circular in shape and was constructed of plastic. The contents of each Container A through D were subsequently sealed in the containers with a lid. Each sealed container A through D was respectively placed in individual containers A1 through D1. Containers A1 through D1 were each filled with the same tap water. Each container A1 through D1 had a diameter of approximately 5½ inches, a height of approximately 2¼ inches, a volume of approximately 54 inches$^3$, was circular in shape and was constructed of plastic. Containers A1 through D1 were subsequently x-rayed and an x-ray film was developed. Based on review of the x-ray film, containers B and C both had a transmission attenuation factor of an amount similar to the attenuation factor of other shields that include barium but do not include foam and a transmission attenuation factor significantly greater than containers A and D.

EXAMPLE 2

An experiment was performed to examine the radiation attenuation effectiveness of a covering or shield (shield 10) having a matrix 320 (see FIGS. 1B through 1E). Matrix 320 includes an attenuating filler and a space 340 within matrix 320. A matrix was produced using the method disclosed in U.S. Pat. No. 4,938,233 issued Jul. 3, 1990 to Orrison, Jr. titled "RADIATION SHIELD", but a relatively large amount of attenuating filler (i.e., barium sulfate) and air was introduced into the matrix. The resulting matrix was subsequently x-rayed and an x-ray film was developed. Based on review of the x-ray film, the resulting matrix had a transmission attenuation factor of greater than 90% at 90-kVp.

According to a preferred embodiment, shield 10 used in the medical field has a durometer value (i.e., a measure of the drape and hand of the shield) in the range from about 5 to about 80 Shore "00", and most preferably in the range of from about 15 to about 40 Shore "00". The placement stability of the shield (measured as a coefficient of sliding friction determined as the tangent of the angle of inclination to induce sliding) can be greater than 0.5 under certain circumstances, is preferably greater than 0.75 or even greater than 1.0, and for specific applications (such as surgical drape or a protective covering for direct contact with a patient) is preferably in excess of 2.0. The shield used in the medical field can have a transmission attenuation factor of at least 50% of a primary 100-kVp x-ray beam. It will be understood by those who review this disclosure that the shield can be used in a variety of applications (e.g., space travel) and that the durometer values, coefficient of sliding friction values and attenuation values can vary according to the particular application.

It is important to note that the use of the term "covering" or "shield" is not meant as a term of limitation, insofar as any "covering", "shield" or like structure having a radiation attenuation use or application is intended to be within the scope of the term. The use of the term "covering" is intended as a convenient reference for any such "covering" or structure, which may also be viewed synonymously with the term "shield" or other like terms used in the medical, industrial, home, office, outer space and other fields. It is also important to note that the use of the term "radiation" is not meant as a term of limitation, insofar as all electromagnetic radiation (e.g., electromagnetic energy having wavelengths of $1.0 \times 10^{-15}$ meters to $1.0 \times 10^6$ meters, radiation from AC power lines, gamma rays, x-rays, cosmic rays, neutrons, etc.) is intended to be within the scope of the term.

Although only a few exemplary embodiments of the present invention have been described in detail in this disclosure, those skilled in the art who review this disclosure will readily appreciate that many modifications are possible in the exemplary embodiments (such as variations in sizes, structures, shapes and proportions of the various elements, values of parameters, or use of materials) without materially departing from the novel teachings and advantages of the invention. Accordingly, all such modifications are intended to be included within the scope of the invention as defined in the appended claims. Other substitutions, modifications, changes and omissions may be made in the design, operating conditions and arrangement of the preferred embodiments without departing from the spirit of the invention as expressed in the appended claims. Those who review this disclosure should recognize that the subject matter recited in any method claims may be performed in any combination and in any sequence.

What is claimed is:

1. A shield for attenuating the flux of electromagnetic radiation from an article, the shield comprising:
    a flexible matrix comprising a foam including a radiation attenuating material, the matrix including at least one space within the matrix;
    whereby the at least one space reduces the weight of the shield without appreciably reducing the attenuating characteristics of the shield.

2. The shield of claim 1, wherein the shield has a transmission attenuation factor of at least 50% primary 100-kVP x-ray beam, a durometer of less than about 100 shore "00" and a coefficient of sliding friction relative to said article of at least 0.15.

3. The shield of claim 1, wherein the matrix is an expandable foam.

4. The shield of claim 1, wherein the matrix is an insulating material.

5. The shield of claim 1, wherein the matrix is a sponge.

6. The shield of claim 1, wherein a gas is provided in the at least one space of the matrix.

7. The shield of claim 1, wherein the attenuating material is barium sulfate.

8. The shield of claim 3, wherein the matrix includes silicone or urethane.

9. A method of making a covering for attenuating the flux of electromagnetic radiation, the method comprising:

providing a flexible matrix including a radiation attenuating material, and providing at least one layer including a space within the matrix;

whereby the space reduces the weight of the covering without appreciably reducing the attenuating characteristics of the covering.

10. The method of claim 9, further comprising providing the matrix as a foam matrix.

11. The method of claim 10, wherein providing the matrix as a foam matrix further includes injecting the foam matrix into the covering.

12. The method of claim 11, further comprising curing the foam matrix.

13. The method of claim 11, further comprising expanding the foam matrix.

14. The method of claim 9, further comprising providing the matrix as a gel.

15. The method of claim 9, wherein the layer comprises a groove.

16. The method of claim 9, wherein the layer comprises a slot.

17. The method of claim 9, wherein the layer is continuous.

18. The method of claim 17, wherein the layer is non-random.

19. The method of claim 11, wherein the layer is disposed between a first foam layer and a second foam layer.

20. The method of claim 19, further comprising injecting the foam.

21. The method of claim 20, wherein the radiation attenuating material includes bismuth.

22. A shield for attenuating the flux of electromagnetic radiation, the shield comprised of a flexible matrix comprising a gel and including an insulating material and a radiation attenuating material, the matrix including at least one space within the matrix, whereby the at least one space reduces the weight of the shield without appreciably reducing the attenuating characteristics of the shield.

23. The shield of claim 22, wherein the gel comprises a visco-elastic material.

24. The shield of claim 23, wherein the gel comprises a hydrogel.

25. The shield of claim 24, wherein the at least one space comprises a bubble.

26. The shield of claim 24, wherein the at least one space is disposed between a first layer of the gel and a second layer of the gel.

27. The shield of claim 22, further comprising a filler in the at least one space.

28. The shield of claim 27, wherein the filler comprises a wax.

* * * * *